United States Patent [19]

Cogburn

[11] Patent Number: 5,168,102
[45] Date of Patent: * Dec. 1, 1992

[54] ENDOCRINE MANIPULATION TO IMPROVE BODY COMPOSITION OF POULTRY

[75] Inventor: Larry A. Cogburn, New London, Pa.

[73] Assignee: University of Delaware, Newark, Del.

[*] Notice: The portion of the term of this patent subsequent to May 29, 2007 has been disclaimed.

[21] Appl. No.: 583,010

[22] Filed: Sep. 14, 1990

Related U.S. Application Data

[63] Continuation-in-part of Ser. No. 521,228, May 9, 1990, abandoned, which is a continuation-in-part of Ser. No. 169,737, Mar. 18, 1988, Pat. No. 4,929,600.

[51] Int. Cl.$^5$ .................. A61K 37/36; A61K 35/55; A61K 31/195
[52] U.S. Cl. .................. 514/2; 514/21; 514/5; 514/12; 514/567; 424/568
[58] Field of Search .................. 514/2, 5, 21, 12, 567; 424/85.8, 568; 530/308

[56] References Cited

U.S. PATENT DOCUMENTS

| | | |
|---|---|---|
| 80,854 | 6/1983 | Pimblett & Snarey . |
| 601,469 | 5/1948 | Jennings . |
| 2,591,107 | 1/1952 | Turnpk et al. ............ 514/5 |
| 4,407,819 | 10/1983 | Kiernan et al. ............ 514/524 |
| 4,493,828 | 1/1985 | Leung et al. ............ 514/19 |
| 4,562,175 | 12/1985 | Chang et al. ............ 514/12 |
| 4,562,197 | 12/1985 | Snarey et al. ............ 514/343 |
| 4,599,229 | 7/1986 | Maccecchini ............ 424/85.8 |
| 4,599,339 | 7/1986 | Maccecchini ............ 424/85 |
| 4,675,189 | 6/1987 | Kent et al. ............ 424/490 |
| 4,686,098 | 8/1987 | Kopchick et al. ............ 424/424 |
| 4,818,531 | 4/1989 | Anderson et al. ............ 514/12 |

FOREIGN PATENT DOCUMENTS

| | | |
|---|---|---|
| 0085036 | 8/1983 | European Pat. Off. ............ 514/2 |
| 0177819 | 4/1986 | European Pat. Off. ............ 514/12 |
| 0192360 | 8/1986 | European Pat. Off. ............ 514/2 |

OTHER PUBLICATIONS

Thorpe, P. E. and W. Ross "The Preparation and Cytoxic Properties of Antibody-toxin Conjugates" Immunological Reviews 62, 1982, p. 121.

C. P. Alfonso and L. A. Cogburn, Hepatic Thyroxine 5'-Monodeiodinase (5'-MDI) Activity in Broiler Chickens Fed Thyroid Active Substances, Poultry Sci. 65(Suppl.1):4 1986).

P. C. Allen and J. P. McMurtry, Changes in Pancreatic Hormones Associated with Coccidiosis, Poultry Sci. 63:1128-1135 (1984).

P. K. Baker et al., Use of a β-Adrenergic Agonist to Alter Muscle and Fat Deposition in Lambs, J. Anim. Sci. 59:1256-1261 (1984).

D. E. Bauman et al., Responses of High-Producing Dairy Cows to Long-Term Treatment with Pituitary Comatotropin and Recombinant Somatotropin, J. Dairy Sci. 68:1352-1362 (1985).

D. H. Beerman et al., Effects of Cimaterol and Fishmeal on Performance, Carcass Characteristics and Skeletal Muscle Growth in Lambs, J. Anim. Sci. 62:370-380 (1986).

P. Bohlen et al., Isolation and Characterization of the Porcine Hypothalamic Growth Hormone Releasing Factor, Biochem. Biophys Res. Comm. 116:726-734 (1983).

M. B. Bolger et al., Molecular Interactions between Thyroid Hormone Analogs and the Rat Liver Nuclear Receptor, J. Biol. Chem. 255:10271-10278 (1980).

S. J. Bowen et al., Influence of Triiodothyronine and Growth Hormone on Growth of Dwarf and Normal Chickens: Interactions of Hormones and Genotype, Comp. Biochem. Physiol. 86A:137-142 (1987).

R. Brazeau et al., Growth Hormone-Releasing Factor from Ovine and Caprine Hypothalamus: Isolation, Se- (List continued on next page.)

Primary Examiner—Douglas W. Robinson
Assistant Examiner—Jean C. Witz

[57] ABSTRACT

The body composition of poultry is improved by a hormonal strategy that includes the step of
increasing plasma levels of thyroid hormone to about 150-250% (normal endogenous $T_3$ hormone level = 100%) during essentially the finishing phase (e.g., for chickens, 3 to 6 or 7 weeks-of-age) by administering (preferably orally) a metabolically-active thyroid hormone of the formula:

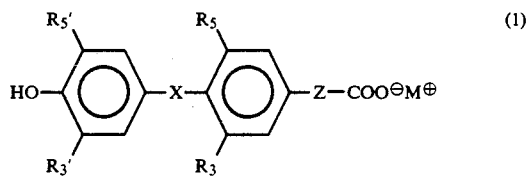

(1)

wherein
X is O, S, or $CH_2$.
Z is $C_2$-$C_4$ alkylene or amino-substituted $C_2$-$C_4$ alkylene,
$M^+$ is a physiologically acceptable cation, $R_3$ and $R_5$ are H or iodo, at least one of them being iodo,
$R_3'$ and $R_5'$ are iodo, or hydrogen or —A—COO—$M^{3\ominus}$, where A is $C_2$-$C_4$ alkylene and $M^{3\ominus}$ is a physiologically acceptable cation,
provided, that when $R_3'$, $R_5'$, $R_3$ and $R_5$ are all iodo, then Z—COO— is the residue of the anion of acetic or propionic acid.

Marked depletion of body fat and increased body protein content are obtained with minimal loss of growth rate or efficiency of feed conversion.

9 Claims, No Drawings

OTHER PUBLICATIONS quence Analysis and Total Synthesis, *Biochem. Biophys. Res. Comm.* 125:606–614 (1984).

F. C. Buonomo and C. A. Baile, Effect of Daily Injections of Growth Hormone–Releasing Factor and Thyrotropin-Releasing Hormone on Growth and Endocrine Parameters in Chickens, *Dom. Anim. Endocrinol.* 4:269–276 (1986).

F. C. Buonomo and C. A. Baile, Recombinant Bovine Somatotropin Stimulates Short Term Increases in Growth Rate and Insulin–Like Growth Factor I (IGF–I) in Chickens, *Dom. Anim. Endocrinol.* 5:219–229 (1988).

F. C. Buonomo et al., Effects of Somatostatin Immunoneutralization on Growth and Endocrine Parameters in Chickens, *Dom. Anim. Endocrinol.* 4:191–200 (1987).

R. H. Dalrymple et al., A Repartitioning Agent to Improve Performance and Carcass Composition of Broilers, *Poultry Sci.* 63:2376–2383 (1984).

Decuypere et al., Effects of Hyper– or Hypothyroid Status on Growth, Adiposity and Levels of Growth Hormone, Somatomedin C and Thyroid Metabolism in Broiler Chickens, *Reprod. Nutr. Develop.* 27:555–565 (1987).

F. Esch et al., Isolation and Characterization of the Bovine Hypothalamic Growth Hormone Releasing Factor, *Biochem. Biophys. Res. Comm.* 117:772–779 (1983).

T. D. Etherton et al., Stimulation of Pig Growth Performance by Porcine Growth Hormone: Determination of the Dose–Response Relationship, *J. Anim. Sci.* 64:433–443 (1987).

R. Guillemin et al., Growth Hormone–Releasing Factor from a Human Pancreatic Tumor that Caused Acromegaly, *Science* 218:585–587 (1982).

R. E. Hammer et al., Expression of Human Growth Hormone–Releasing Factor in Transgenic Mice Results in Increased Somatic Growth, *Nature* 315:413–416 (1985a).

R. E. Hammer et al., Production of Transgenic Rabbits, Sheep and Pigs by Microinjection, *Nature* 315:680–683 (1985b).

S. Harvey, J. Thyroid Hormones Inhibit Growth Hormone Secretion in Domestic Fowl, *Endocrinol.* 96:329–334 (1983).

S. Harvey and S. C. Scanes, Purification and Radioimmunoassay of Chicken Growth Hormone, *J. Endocrinol.* 73:321–329 (1977).

R. L. Hazelwood, Pancreatic Hormones, Insulin/Glucagon Molar Ratios, and Somatostatin as Determinants of Avian Carbohydrate Metabolism, *J. Exp. Zool.* 232:647–652 (1984).

R. L. Hazelwood, Peripheral Endocrine Secretions and Carbohydrate Metabolism, in *Avian Physiology* (P. D. Sturkie ed.) Springer–Verlag, pp. 303–325 (1986).

Hervas et al., Rapid Effects of Single Small Doses of L-Thyroxine and Triiodo–L-Thyronine on Growth Hormone, as Studied in the Rat by Radioimmunoassay, *Endocrinology* 97:91–101 (1975).

F. C. Leung et al., Thyrotropin-Releasing Hormone Stimulates Body Weight Gain and Increases Thyroid Hormones and Growth Hormone in Plasma of Cockerels, *Endocrinology* 115:736–740 (1984).

J. D. May, Effect of Dietary Thyroid Hormone on Growth and Feed Efficiency of Broilers, *Poultry Sci.* 59:888–892 (1980).

J. D. Day, Effect of Dietary Thyroid Hormones on Serum Hormone Concentration, Growth, and Body Composition of Chickens, *Aspects of Avian . . . Implications*, (C. G. Scanes et al., eds.) Tex. Tech. Univ. Press 26:185–189 (1982).

R. D. Palmiter et al., Dramatic Growth of Mice that Develop from Eggs Microinjected with Metallothionein–Growth Hormone Fusion Genes, *Nature* 300:611–615 (1982).

R. D. Palmiter et al., Metallothionein–Human GH Fusion Genes Stimulate Growth of Mice, *Science* 222:809–814 (1983).

J. P. Peters, Consequences of Accelerated Gain and Growth Hormone Adminiatration for Lipid Metabolism in Growing Beef Steers, *J. Nutr.* 116:2490–2503 (1986).

J. A Proudman, Recombinant-Derived Chicken Growth Hormone Used for Radioimmunoassay, *Proc. Soc. Exp. Biol. Med.* 175:417–419 (1984).

K. L. Raheja et al., Elevated Insulin/Glucagon Ratios and Decreased Cyclic AMP Levels Accompany the Glycogen and Triglyceride Storage Syndrome in the Hypotyroid Chick, *Horm. Metab. Res.* 12:51–55 (1980).

C. G. Scanes, et al., Abnormalities in the Plasma Concentrations of Thyroxine, Tri-iodothyronine and Growth Hormone in Sex–Linked Dwarf and Autosomal Dwarf White Leghorn Domestic Fowl (Gallus Domesticus), *J. Endocrinol.* 97:127–135 (1983).

C. G. Scanes et al., Synthetic Human Pancreatic Growth Hormone Releasing Factor (GRF) Stimulates Growth Hormone Secretion in the Domestic Fowl (*Gallus Domesticus*), *Life Sci.* 34:1127–1134 (1984).

C. G. Scanes et al., Effect of Chicken Growth Hormone Triiodothyronine and Hypophysectomy in Growing Domestic Fowl, *Growth* 50:12–31 (1986).

C. G. Scanes et al., Stimulation of In-Vivo Growth Hormone Secretion in Young Chickens by Rat Hypothalamic Growth Hormone–Releasing Factor and Synthetic Analogues, *J. Endocrinol.* 108:412–416 (1986).

G. S. G. Spencer et al., The Effect of Immunization Against Somatostatin on Growth Rates and Growth Hormone Secretion in the Chicken, *Comp. Biochem. Physiol.* 85A:553–556 (1986).

J. Spiess et al., Characterization of Rat Hypothalamic Growth Hormone–Releasing Factor, *Nature* 303:532–535 (1983).

L. M. Souza et al., Application of Recombinant DNA Technologies to Studies on Chicken Growth Hormone, *J. Exp. Zool.* 232:465–473 (1984).

H. R. Wilson et al., Abdominal Fat Pad Reduction in Broilers with Thyroactive Iodinated Casein, *Poultry Sci.* 62:811–818 (1983).

D. F. Wise et al., Growth Performance and Carcass Merit of Lambs Treated with Growth Hormone Releasing Factor (GRF) or Somatotropin (ST), *J. Anim. Sci.* 66(Suppl.1):275 (1988).

May, Aspects of Aviai Endoceinology, Grad. Studies Texas Tech Univ. 26:185–189 (1982).

Dracupypcre et al. Reprod. Nutr. Develop. 27(2B):555–565 (1987).

Stewart et al CA100:171797 (1984).

ENDOCRINE MANIPULATION TO IMPROVE BODY COMPOSITION OF POULTRY

This application is a continuation-in-part of Ser. No. 07/521,228, now abandoned, which is a continuation-in-part of Ser. No. 07/169,737, now U.S. Pat. No. 4,929,600.

BACKGROUND OF THE INVENTION

This invention relates to a method for improving the carcass quality of poultry. An aspect of this invention relates to a manipulation of the hormone system of the poultry. Still another aspect of this invention relates to means and methods for altering blood levels of hormones in the bodies of poultry, which means and methods can be employed on a commercial scale.

DESCRIPTION OF THE PRIOR ART

A predominant cost in intensive production of poultry is the feed energy required for metabolism and growth. The metabolizable energy derived from feedstuffs is partitioned into energy for maintenance (i.e., thermoregulation and nutrient utilization) and the energy assimilated into animal product (meat or eggs). Advances in genetics, nutrition and management have provided producers with rapidly growing poultry produced for meat (broiler chickens, turkeys, and the like) that efficiently convert feed energy and nutrients into animal product. Unfortunately, excessive fat deposition is an undesirable consequence of the accelerated growth of poultry and high nutrient density of poultry rations. As the poultry reach market age, fat deposition-rather than protein accretion-becomes the principal component of weight gain. For example in broiler chickens, body fat represents from 7 to 20% of live market weight, with abdominal fat making up about 4% of total body weight. Since accumulation of excessive body fat is considered an economic loss to both the producer and consumer of poultry meat, recent research efforts have attempted to solve the problem of excessive fat deposition in the chicken's body. The inter-dependence of nutritional and genetic factors that determine accumulation of body fat precludes a uniform strategy for nutritional restriction of fat deposition. Futhermore, genetic selection against body fat would probably reduce live market weight as well as carcass quality.

Metabolically-active agents, such as hormones, appear to have the greatest potential for manipulating fat deposition and/or muscle development in animals raised for meat (see Kiernan et al., U.S. Pat. No. 4,407,819 issued Oct. 4, 1983). For example, injection of finishing pigs with purified porcine growth hormone (pGH) was found to increase growth rate by 10–14%, improve feed conversion by 7–19%, reduce carcass fat content by 18–25% and increase muscle mass by 24–36% (T. D. Etherton et al., *J. Anim. Sci.* 64:433–443, 1987). Similarly, daily administration of natural or recombinant-derived bovine GH (bGH) to dairy cows can increase milk yield by 23 to 41% (D. E. Bauman et al., *J. Dairy Sci.* 68:1352–1362, 1985).

In contrast, however, these discoveries are not easily applied to poultry. Daily injection of broiler chickens with natural or recombinant-derived chicken GH (cGH) does not stimulate growth; in fact, cGH treatment usually results in increased accumulation of body fat (F. C. Leung et al., *Endocrinology* 118:1961–1965, 1985; S. S. Liou et al., *Poultry Sci.* 64(Suppl. 1):136, 1985; W. H. Burke et al., *Endocrinology*, 1987). Apparently, endocrine regulation of growth and metabolism in domestic fowl is distinctly different from that described for food mammals since exogenous cGH treatment alone does not promote growth or improve productive efficiency. The following summary of the relevant poultry science literature provides some insight into the comlexity of the research findings in this field.

Earlier work suggested that a synthetic iodinated protein, possessing thyroxine ($T_4$) activity, could be used as a feed additive to increase egg production or growth rate of domestic fowl (H. W. K. Jennings, British Patent 601,469, published in May of 1948). Iodinated casein (i.e., protomone) with 1% $T_4$ activity was originally developed as a possible growth promoter for poultry and livestock. However, the incorporation of protomono into the feed of meat-type chickens depressed growth rate, reduced feed efficiency, lowered carcass quality, and increased mortality rate when fed throughout the growth cycle (H. R. Wilson et al., *Poultry Sci.* 62:811–818, 1983).

Triiodothyronine ($T_3$) and $T_4$ can be directly incorporated into the feed of broiler chickens for the purpose of elevating serum or plasma levels of thyroid hormones (J. D. May, *Poultry Sci.* 59:888–892, 1980; J. D. May in *Aspects of Avian . . . Implications* (C. G. Scanes et al., eds.) Texas Tech Univ. Press 26:185–189, 1982). This work has shown that treatment of normal broiler chickens with 0.25 to 1 parts per million (ppm) of dietary $T_3$ throughout the entire growth cycle reduced body weight gain and feed efficiency. In contrast, the same doses of dietary $T_4$ did not impair growth performance. The depressed growth rate and reduced feed efficiency of normal (euthyroid) broiler chickens fed 1 ppm $T_3$ throughout the growth cycle has led to the notion that dietary $T_3$ is detrimental to the growth and productive efficiency of poultry.

Attempts at using administration of exogenous GH to stimulate the growth of normal chickens have generally been unsuccessful. Daily intravenous injection of thyrotropin-releasing hormone (TRH) (1 or 10 μg/kg of body weight/day) or GH-releasing factor (GRF, 10 μg/kg of body weight/day) alone or in combination for 21 days failed to stimulate growth rate or improve feed efficiency of broiler chickens despite elevated plasma GH levels (F. C. Buonomo and C. A. Baile, *Dom. Anim. Endocrinol.* 4:269–276, 1986). Most of the evidence for supporting the idea that exogenous GH is capable of promoting growth of broiler chickens is derived from studies on growth-compromised Leghorn (egg-type) chickens. In these studies, dwarf strains or hypophysectomized (i.e., pituitary gland surgically removed) Leghorns were given replacement doses of $T_3$, $T_4$ or GH (usually mammalian GH) alone or GH in combination with either $T_3$ or $T_4$ to determine the importance of these hormones in the normal growth process. The sex-linked dwarf Leghorn chicken has elevated plasma levels of both GH and $T_4$ whereas $T_3$ concentrations are greatly reduced. The depressed growth rate in dwarf strains of Leghorn chickens was restored to normal by supplementing their diets with either $T_3$ or $T_4$, or by the combination of $T_4$ with a daily injection of mammalian GH (J. A. Marsh et al., *Proc. Soc. Exp. Biol. Med.* 177:82–91, 1984; and J. A. Marsh et al., *Proc. Soc. Exp. Biol. Med.* 175:351–360, 1984). The importance of $T_3$ to the normal growth process was further demonstrated by the ability of exogenous $T_3$, rather than GH therapy, to correct the growth deficit of hypophysectomized Leghorn chickens (C. G. Scanes et al., *Growth* 50:12–31, 1986). Although several studies have revealed distinct interactions between GH and the thyroid hormones in regulation of growth in chickens, this area clearly needs further research to develop a truely practical program of hormone manipulation which is useful on a commercial scale for normal, meat-type poultry.

Any hormonal treatment that restricts fat deposition while increasing carcass protein content could theoretically have a major impact on the cost and quality of poultry meat, and the formulation of poultry rations, but because poultry (particularly broiler chickens) are produced on such an enormous commercial scale, the treatment must satisfy a variety of practical criteria.

DEFINITIONS

Throughout this application, the following terms are used with the meanings indicated below.

"Finishing phase" or "finishing phase of the growth cycle" means the time period in the production of poultry after the major portion of the rapid growth of the avian species (e.g. broiler chickens and turkeys) has been completed. With modern broiler chicken production techniques, chickens grow to a high percentage of their live market weight in the first three to four weeks of life. Six or seven weeks of age is usually considered a market age for broiler chickens. Thus, the "finishing phase" for broiler chickens typically begins at about 3, 4 or (rarely) 5 weeks of age and lasts until slaughter, or a least until marke age. In some embodiments of this invention, it may be desirable to permit the poultry to clear their bodies of any treatment for up to a week or so prior to slaughter. Thus, the "finishing phase" for broiler chickens can last as little as two weeks or as long as about five weeks, but in any case the rapid growth phase has been substantially completed before the "finishing phase" is underway. For turkeys, the growth cycle lasts longer (e.g. 15 to 25 weeks), hence the "finishing phase" begins after 6 weeks of age and may last longer than four or five weeks. It has now been found that circulating levels of endogenous $T_3$ (3,3',5-triiodo-L-thyronine) decrease during the "finishing phase" (as defined herein). Indeed, there is a very rapid rate of decline in plasma $T_3$ during this period. Accordingly, another way of defining the "finishing phase" of this invention is to test for the peak in endogenous plasma $T_3$, because the "finishing phase" of growth begins substantially immediately thereafter.

"Metabolically-active thyroid hormone" refers to the natural or synthetic iodinated D- or L- or DL-thyronine compounds or iodinated phenoxyphenol-substituted aliphatic carboxylic acids having more than 50% of the receptor binding capability of $T_3$ (3,3',5-triiodo-L-thyronine, alternatively 0-[4-hydroxy-3-iodophenyl]-3,5-diiodo-L-tyrosine) and preferably at least 30% of the in vivo activity of $T_3$. "Receptor binding" is defined herein in accordance with M. B. Bolger et al., *J. Biol. Chem.* 255:10271–10278 (1980). Preferred metabolically-active thyroid hormones are compounds of the formula I:

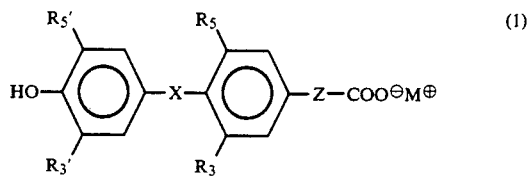

where Z is $C_2$–$C_4$ alkylene or amino-substituted $C_2$–$C_4$ alkylene;

$M^+$ is a physiologically acceptable cation such as $H^+$;

$R_3$ and $R_5$ are hydrogen or iodine, at least one of them being iodine;

$R_3'$ and $R_5'$ are hydrogen or iodine or —A—COO$^-M^+$, where A is $C_2$–$C_4$ alkylene and $M^+$ is a physiologically acceptable cation; and X is a bridging radical such as —CH$_2$—, —S— or —O— (preferably —O—); provided, that if $R_3'$, $R_5'$, $R_3$ and $R_5$ are all iodine (I), then Z—COO$^-$ is a residue of the anion of acetic or propionic acid. The most active compounds of formula I are $T_3$ itself, "Triac" (Z=CH$_2$, M=H, $R_3$, $R_5$ and $R_3'$=I, $R_5'$=H) and "Tetrac" (similar to "Triac", except that $R_5'$=I). When Z is amino-substituted, the radical —Z—COO$^-$ can be the residue of D- or L- or DL-alanine.

BRIEF DESCRIPTION OF THE INVENTION

This invention is concerned with a novel, practical hormonal treatment for poultry grown for meat production, particularly broiler chickens, that reduces carcass fat and increases carcass protein content, without substantially detracting from normal growth. The treatment comprises a carefully timed addition of about 0.01–3 parts per million of diluent (e.g. feed), i.e. 0.01–3 ppm, preferably 0.1 to 1 ppm of metabolically-active thyroid hormone, depending generally upon the activity of the thyroid hormone, the degree of decrease in fat deposition desired, the degree of deviation from normal growth which can be tolerated, etc. The preferred metabolically active thyroid hormone is triiodothyronine ($T_3$, 3,3',5-triiodo-L-thyronine or 0-[4-hydroxy-3-iodophenyl]-3,5-diiodo-L-tyrosine), and the preferred route of administration is oral; accordingly, it is particularly preferred to add the metabolically active thyroid hormone to the feed of broiler chickens. It is important that the metabolically-active thyroid hormone be given during the finishing phase (usually 3 to 7 weeks-of-age). The consumption of feed containing the preferred amount of $T_3$ provides broiler chickens with a 50 to 150% elevation of plasma $T_3$ levels when compared to controls. The efficacy of this invention is enhanced when, in addition to providing poultry with dietary $T_3$ during the finishing phase, GH (somatotropin) or glucagon levels in the bloodstream are also increased, or glucagon levels are increased relative to insulin levels, also during the finishing phase and preferably by 2- to 10-fold. In one embodiment of this invention, poultry are provided with dietary $T_3$ during the finishing phase and circulating levels of glucagon relative to insulin are increased, i.e., the insulin-to-glucagon (I/G) molar ratio is decreased. Since the timing of applying the dietary $T_3$ treatment alone or dietary $T_3$ in combination with other metabolically-active hormones (e.g. cGH or glucagon) to broiler chickens is of very great significance and should be substantially limited to the finishing phase, the rapid growth phase of the chickens should be substantially concluded when the treatment begins, and treatment will typically last for two to five weeks. When the timing of dietary metabolically-active thyroid hormone is controlled in accordance with this invention, and when the amount of this hormone is selected in accordance with criteria described subsequently, no statistically significant impairment of growth is observed. Although reduction in body fat is maximized when the thyroid hormone treatment is combined with GH enhancement (e.g. by administration of GH or GH-releasing factor) or decrease in the insulin/glucagon (I/G) ratio, a 17-25% reduction in body fat can be obtained with finishing-phase thyroid hormone administration alone. This result is surprising in view of previous experience with $T_3$ given throughout the growth cycle of the birds.

This invention is not bound by any theory. Available data suggest that metabolically active thyroid hormone manipulation within the scope of this invention can have a useful effect upon several variables such as I/G molar ratio of the avian pancreatic hormonal system, accretion and/or degration of protein. It is presently theorized that a decrease in the I/G molar ratio of poultry during the finishing phase mobilizes body fat stores, and, if a carefully controlled amount of metabolically-active thyroid hormone is used, body fat content is reduced. In the case of $T_3$ specifically, the optimum range of content in feed appears to be about 0.1 to 1 ppm.

DETAILED DESCRIPTION OF THE INVENTION

The above mentioned metabolically-active hormones are naturally synthesized within the body of domestic fowl and are known to be important regulators of various metabolic activities (i.e., energy, carbohydrate, lipid and protein metabolism) that contribute to normal growth and development. Within the scope of this invention, there are three major groups of metabolically-active hormones: (1) pituitary hormones [GH, prolactin and thyroid-stimulating hormone (TSH)] and their hypothalamic releasing factors [GH-releasing factor (GRF), GH-release inhibiting factor or somatostatin (SRIF), and thyrotropin-releasing hormone (TRH)], (2) the thyroid hormones ($T_3$ and $T_4$), and (3) the pancreatic hormones (insulin, glucagon and somatostatin). The natural metabolically-active hormones, synthetic analogues and their pharmacologically-acceptable salts are to be considered within the scope of this invention. Amino acid components or residues and carbohydrate components of synthetic metabolically-active substances are generally provided in the most active isomeric forms (e.g. L-amino acids, D-carbohydrates, etc.), except that racemates (DL-compounds), diastereomers, etc. can be used when sufficient normal physiological activity is still obtained, e.g. 50% of the active (D- or L-) form. Analogs of $T_3$ containing a D-amino acid residue can be active, apparently because of the importance of the location of other substituents on the molecules. This invention is concerned with means of enhancing circulating blood levels of certain metabolically-active hormones including the thyroid hormones (particularly $T_3$). In some embodiments of the invention GRF or GH or pancreatic hormone levels are also manipulated.

The secretion of trophic hormones from the pituitary gland is regulated by releasing or inhibiting factors secreted by the hypothalamus. Within the scope of this invention, the releasing factors that regulate secretion of TSH and pituitary GH (somatotropin) are of particular interest. Thyrotropin-releasing hormone (TRH) stimulates the release of both TSH and GH from the avian pituitary gland into the bloodstream. Under the stimulating effect of TSH, the thyroid gland predominately synthesizes and secretes $T_4$ (3,5,3',5'-tetra-iodothyronine) into blood. The enzymatic activity of thyroxine-5'-monodeiodinase in peripheral tissue (particularly the liver and kidney) is responsible for converting $T_4$ into metabolically-active $T_3$. The positive or stimulative pathway is represented by: TRH→pituitary→TSH→thyroid→$T_4$→5'-monodeiodinase activity→$T_3$. It is generally accepted that $T_4$ is a prohormone without significant metabolic activity and that any benefit derived from treatment of animals with exgenous $T_4$ is derived from its conversion, via 5'-monodeiodinase activity, into metabolically-active $T_3$. Thus, the attempts at stimulating the growth or productive efficiency of domestic animals (poultry and livestock) with iodinated protein (i.e., protomone) that is based on thyroxine activity (see Jennings, British Patent 601,469 dated May 6, 1948) are of questionable efficacy since thyroxine ($T_4$) is essentially inactive in provoking metabolic and hormonal responses. In birds, circulating $T_3$ levels play an important role in regulating metabolic heat production and secretion of pituitary and pancreatic hormones. It is apparent from the working Examples which follow that $T_3$ also regulates the secretion of insulin and glucagon from the avian pancreas. All embodiments of this invention have in common the oral (preferably dietary) administration of metabolically-active thyroid hormone (preferably $T_3$ or a compound of Formula I, above, which has biological activity comparable to $T_3$) to poultry during the finishing phase, but not significantly prior to the finishing phase. During the finishing phase, the GH (somatotropin) naturally secreted by the poultry has already done much of its work, and there is no significant losses in body weight or protein content during this phase. There is, on the other hand, a more rapid utlization of body fat as a result of the orally-administered Formula I compound.

The other embodiments of this invention enhance or even synergize effectiveness of the metabolically-active thyroid hormone treatment by increasing blood levels of GH or by decreasing the insulin/glucagon (I/G) molar ratio. The timing of this enhancement effect need not be exactly coextensive with the metabolically-active thyroid hormone treatment, but it is believed to be useful to decrease the I/G molar ratio during the finishing phase, and insofar as GH also may depress the I/G molar ratio, GH treatment is also most useful during the finishing phase. In administring GH, it is preferred to match as closely as possible the natural timing of the pituitary release of this hormone, which follows a pattern characterized by a series of prominent peaks spaced an hour or two apart from one another.

One method of enhancing blood levels of GH is by administration of the hypothalamic releasing factors that provoke endogenous GH secretion from the pituitary gland. Human GRF is a 44 amino acid polypeptide hormone with a molecular weight of 5040 (R. Guillemin et al., *Science* 218:585-587, 1982) that stimulates endogenous GH secretion from the pituitary gland (see Chang et al. U.S. Pat. No. 4,562,175 issued Dec. 31, 1985). Subsequent to the isolation and characterization of human GRF, the amino sequence has been determined for rat (J. Spiess et al., *Nature* 303:532-535, 1983), porcine (P. Bohlen et al., *Biochem. Biophys. Res. Comm.* 116:726–734, 1983), bovine (F. Esch et al., *Biochem. Biophys. Res. Comm.* 117:772–779, 1983), caprine, and ovine (P. Brazeau et al., *Biochem. Biophys. Res. Comm.* 125:606–614, 1984) forms of GRF. Apparently only the first 29 amino acids (i.e., GRF 1–29) are required for GH-releasing activity; therefore, numerous synthetic analogues have been developed that range from GRF 1–29 to GRF 1–44. Although an avian GRF has not yet been isolated and characterized, a number of these analogues possess the ability to provoke endogenous GH secretion from the chicken's pituitary (C. G. Scanes et al., *Life Sci.* 34:1127–1134, 1984; and C. G. Scanes et al., *J. Endocrinol.* 108:413–416, 1986). Within the context of this invention are all the pharmaceutical acceptable salts of the natural, recombinant-derived and synthetic analogues of GRF which stimulate GH secretion from the avian pituitary gland. The route of administration of GH or GRF can be oral, parenteral or by prolonged-release implant. Instead of administering cGH, a 191 amino acid protein hormone, exogenous GRF (a polypeptide hormone ranging from 1–29 to 1–44 amino acids) can be used to increase endogenous cGH secretion.

a MT-GH fusion gene) results in a dramatic increase in body growth due to hypersecretion of GH (R. D. Palmiter et al., *Nature* 300:611–615, 1982; and R. D. Palmiter et al., *Science* 222:809–814, 1983). These transgenic mice typically show increases of 100- to 800-fold in serum GH levels and grow to twice the normal body size. Thus, gene insertion technology has tremendous potential for selective growth stimulation and/or improvements in productive efficiency of domestic animals. In fact, transgenic rabbits, pigs and sheep have been produced by microinjection of the MT-GH fusion gene (R. E. Hammer et al., *Nature* 315:680–683, 1985). Furthermore, the introduction of a MT-GRF fusion gene into mice also results in increased body growth in the MT-GRF transgenic mice due to hypersecretion of GRF and, consequently, increased secretion of pituitary GH (R. E. Hammer et al., *Nature* 315:413–416, 1985). However, the nature of ovulation and fertilization of the ovum in birds does not allow microinjection of hybrid fusion genes into the fertilized ovum. Souza et al. (*J. Exp. Zool.* 232:465–473, 1984) have developed a recombinant retrovirus (i.e., a Rous sarcoma virus) vector that contains the entire coding region for cGH (designated SRA-cGH9). Infection of 9-day-old

| Human Growth Hormone-Releasing Factor |
|---|
| 10 20 30 |
| 1 Y A D A I F T N S Y R K V L G Q L S A R K L L Q D I M S R Q |
| 31 Q G E S N Q E R G A R A R L-NH$_2$ |

| Composition | | | | | | | | | |
|---|---|---|---|---|---|---|---|---|---|
| 5 | ALA | A | 5 | GLN | Q | 5 | LEU | L | 4 | SER | S |
| 6 | ARG | R | 2 | GLU | E | 2 | LYS | K | 1 | THR | T |
| 2 | ASN | N | 3 | GLY | G | 1 | MET | M | 2 | TYR | Y |
| 2 | ASP | D | 2 | ILE | I | 1 | PHE | F | 1 | VAL | V |

Mol. wt = 5040
Number of residues = 44
R. Guillemin et al., Science 218:585–587, 1982

Another method of enhancing endogenous GH secretion in domestic fowl is the use of TRH-a tripeptide releasing factor (pyro-L-Glu-L-His-L-Pro-NH$_2$) secreted by the hypothalamus that provokes the secretion of GH and TSH from the avian pituitary. Daily intravenous injection of 1 to 10 μg TRH/day from 4 to 6 or 8 weeks-of-age is capable of increasing the growth rate of broiler chickens (Leung et al., U.S. Pat. No. 4,493,828 issued Jan. 15, 1985). An obvious advantage of using TRH treatment as a means of enhancing GH secretion in broiler chickens is that this hypothalamic releasing factor is orally-active and can be incorporated into the feed or drinking water of poultry (Snarey et al., U.S. Pat. No. 4,562,197, issued Dec. 31, 1985). The disadvantage of this approach of stimulating GH secretion is that TRH is a non-selective releasing factor which provokes the release of at least two pituitary hormones (i.e., TSH and GH). Within the scope of this invention is the use of orally-active TRH or its analogs applied in either the feed or drinking water of poultry to increase GH secretion during the finishing phase of the growth cycle.

Still another method of enhancing circulating blood levels of GH is the introduction of a fusion gene into somatic tissue or the germ line of poultry which leads to expression of copious amounts of GH in circulation or greater expression of GRF (i.e., production of "transgenic chickens"). The microinjection of fertilized mouse ova with a hybrid fusion gene carrying the metallothionein (MT) promoter region and the structural gene which codes for either rat or human GH (i.e., chicken embryos with the SRA-cGH9 retrovirus vector resulted in 3- to 10-fold increases in serum GH levels in the hatched chickens.

It is therefore within the scope of this invention to feed (within the specific timing guidelines of this invention) a metabolically active thyroid hormone to "transgenic chickens" which carry a hybrid fusion gene for enhancing blood levels of GRF or GH.

One embodiment of this invention involves the manipulation of the molar ratio of insulin-to-glucagon (I/G) secreted into blood by the endocrine pancreas. Endocrine regulation of metabolism in birds is distinctly different from that of mammals because glucagon is the pancreatic hormone that regulates blood glucose levels in birds, and because fat synthesis (i.e., lipogenesis) takes place in the liver of birds (R. L. Hazelwood, in *Avian Physiology*. P. D. Sturkie, ed., Springer-Verlag, pp. 303–325, 1986). In birds, glucagon exerts a strong catabolic action by mobilizing free fatty acids from adipose tissue (i.e., a lipolytic action) whereas insulin promotes anabolic activities (i.e., glucose uptake, the formation and storage of glycogen, etc.). Thus, the I/G molar ratio serves as the prime determinant of metabolic homeostasis in birds (R. L. Hazelwood, *J. Exp. Zool.* 232:647–652, 1984). A high I/G molar ratio indicates that the bird is in an anabolic mode (i.e., nutrient storage) while a low I/G molar ratio reflects the catabolic state (i.e., nutrient utilization). The avian pancreas also produces an exceptionally large quantity of SRIF which is thought to be an important regulator of the I/G molar ratio. Of particular interest is the fact that pancreatic SRIF is a potent inhibitor of glucagon secretion in chickens; therefore, it appears that immunoneutralization of SRIF, designed to promote pituitary GH secretion, can also enhance glucagon secretion from the pancreas.

Experimentation carried out in support of this invention indicates that administration of exogenous ncGH by injection and $T_3$ by dietary treatment during the finishing phase of the chicken's growth cycle ultimately alters the I/G molar ratio. The metabolic events that lead to the dramatic depletion of body fat content are brought about by a reduction in the I/G molar ratio (i.e., reduced insulin and elevated glucagon levels in blood) and an increase in circulating $T_3$ levels. This concept is supported by the observation that dietary $T_3$ treatment alone depresses insulin secretion while glucagon secretion is increased (i.e., a reduced I/G molar ratio) and consequently decreases fat deposition in chickens. Treatment of chickens with propylthiouracil, a goitrogen that inhibits 5'-monodeiodinase activity and therefore the conversion of $T_4$ into $T_3$, induces a hypothyroid state that results in elevated plasma insulin levels and increased accumulation of body fat (K. L. Raheja et al., Horm. Metab. Res. 12:51-55, 1980; and Example 1 below). Furthermore, there is sufficient experimental evidence to support the idea that providing poultry with dietary $T_3$ and exogenous glucagon (by injection, implant or orally-active analogues of glucagon) would achieve the same benefits and improvements in body composition as the combination of dietary $T_3$ with any other treatment that simultaneously enhances circulating GH concentrations. This invention contemplates the use of exogenous glucagon treatment in combination with dietary $T_3$ as the most simple version of an endocrine manipulation designed to reduce body fat content of poultry.

Glucagon is a highly conserved polypeptide hormone which has an identical amino acid sequence among mammals. Chicken and turkey glucagon differ from mammalian glucagon by the single substitution of serine (SER) for asparagine (ASN) at position 28 (R. L. Hazelwood, J. Exp. Zool. 232:647-652, 1986). The amino acid sequence of duck glucagon differs from other birds (chicken and turkey) due to the single substitution of threonine (THR) for serine (SER) at position 16. Because of these structural similarities, the commercial preparations of glucagon from the pancreases of slaughtered cattle and swine have the same biological and metabolic activity as endogenous glucagon when injected into chickens.

have the opposite effect in avian species; that is, they decrease the I/G molar ratio. Any agent which decreases the I/G molar ratio in birds can be substituted for exogenous glucagon treatment in this invention.

Because of the ease and convenience of administration of orally-active hormones or hormone stimulants or suppressants through poultry feed, one of the embodiments of this invention involves a finishing feed which contains physiologically effective amounts of metabolically-active thyroid hormone (preferably $T_3$), alone or in combination with other orally-active compounds which stimulate or suppress hormone secretion. Finishing feeds typically contain a major amount (e.g. 60-90% by weight) of ground-up grain (corn, soybeans, etc.), a modest amount of fat (e.g. <10%), salts, vitamin and mineral premixes, amino acids, etc. The protein content is typically above 15% (e.g. 17-25% by weight), and some fiber content should be present.

Regardless of which embodiment of this invention is used, no radical changes in feed compositions or daily ration weights are necessary; indeed, conventional finishing feed formulas and amounts (except for the addition of dietary thyroid hormone and, if desired, orally active GH- or glucagon-increasing agents) are fully operative in this invention. The health of the birds does not appear to be adversely affected, and essential body functions (e.g. thermoregulation) do not appear to be adversely affected. However, economically advantageous changes in energy and/or protein content of finishing feeds are made possible by this invention.

Referring now to broiler chickens as a benchmark for the beneficial effects of this invention, it must be noted that these chickens grow from a weight of 30 to 50 grams at hatching to about 1.5-3 or even as much as 5 kilograms of body weight at market age. Of this market weight, 15-20 wt.-% is protein, 2-3 wt.-% is inorganic (showing up as ash in proximate analysis of body composition), and more than 10 wt.-% (e.g. 10-20 wt.-%) is fat, which means that the protein:fat ratio (by weight) is likely to be at or below 1.5:1 and certainly well below 2:1. In broiler chickens treated according to this invention, however, protein:fat ratios above 1.6:1 and even above 2:1 have been obtained, due to decreases in carcass fat content exceeding 15 wt.-%. A comparable increase in the protein:fat ratio was not obtained with $T_4$+GH treatment (although some improvement was found); $T_4$ treatment alone had almost no effect upon this ratio; and various other treatments actually seemed to decrease the protein:fat ratio at the doses tested (e.g. GH alone, TRH alone, TRH+GH, and propylthiouracil alone).

CHICKEN GLUCAGON

| | 10 | | | 20 | | | 30 | |
|---|---|---|---|---|---|---|---|---|
| 1 H S Q G T F T S D Y S K Y L D S R R A Q D F V Q W L M S T | | | | | | | | |

| | | | Composition | | | | | | | | |
|---|---|---|---|---|---|---|---|---|---|---|---|
| 1 | ALA | A | 3 | GLN | Q | 2 | LEU | L | 2 | PHE | F | 1 | TRP | W |
| 2 | ARG | R | 1 | GLY | G | 1 | LYS | K | 5 | SER | S | 2 | TYR | Y |
| 3 | ASP | D | 1 | HIS | H | 1 | MET | M | 3 | THR | T | 1 | VAL | V |

Mol. wt. = 3,485
Number of residues = 29
R. L. Hazelwood, "Carbohydrate Metabolism", in Avian Physiology, P. D. Sturkie ed., Academic Press, pp. 303-325, 1986.

Orally-active drugs have been developed for increasing the I/G molar ratio in mammals, e.g. to combat certain mild forms of diabetes. Some of these drugs

DOSAGE OF METABOLICALLY ACTIVE THYROID HORMONE

As noted previously, the preferred dosage of exogenous metabolically active thyroid hormone (e.g. the concentration of $T_3$ in finishing feed) is a variable which depends upon a variety of objectives and parameters such as effectiveness of the thyroid hormone, the desired degree of control over fat accretion, the desired degree of protein accretion, the degree of deviation from normal growth which can be tolerated, and the like. The receptor binding capacity thyroid hormones useful in this invention can vary from 50% ($T_3 = 100\%$) to well in excess of 100%. Some synthetic $T_3$ analogs are more active than $T_3$ itself by a factor of three or four. Accordingly, any of these highly active analogs, used as feed additives, can be present to the extent of only about 0.01 parts per million of the feed and still have a measurable effect upon fat accretion. At the other extreme, a $T_3$ analog or a $T_3$ racemate with less than the activity of $T_3$ (e.g. 50% of the receptor binding capacity) could be present at levels up to 3 ppm of feed without causing intolerable or unacceptable effects upon weight gain or body composition.

Using $T_3$ itself as a standard, the preferred content or dose finishing feed is preferably much less than 3 ppm, because some deviation from normal weight gain is observed even at 1 ppm dose. At 0.1 ppm, on the other hand, no significant adverse effect upon weight gain can be detected, yet the protein content of the carcass is improved relative to fat content. The increased protein accretion appears to be due to decrease in fat deposition combined with a good protein Fractional Accretion Rate (FAR). Protein FAR is determined by measuring the Fractional Synthesis Rate (FSR) and Fractional Degradation Rate (FDR) and finding the difference between these rates, i.e.

$$FAR = FSR - FDR$$

At very low dosages of exogenous $T_3$ (e.g. 0.1 to 0.5 ppm, based on the weight of the finishing feed), protein FAR is close to or within normal limits or enhanced (despite the tendency of $T_3$ to depress GH levels), and fat deposition is suppressed. A dosage of 0.25 parts $T_3$ per million parts of feed presently appears to be very close to optimum, because the protein accretion rate was higher, the body fat of the birds is decreased by as much as 20 to 25%, and virtually no statistically significant adverse effect on growth rate is observed.

The consumption of finishing feed containing $T_3$ or a metabolically active $T_3$ analog appears to elevate plasma thyroid hormone levels in a dose-dependent manner. In the case of $T_3$, a typical dose-response relationship is as follows.

| Amount of $T_3$ in feed | Plasma $T_3$ level (control group = 100% of normal) |
| --- | --- |
| 0 ppm | 100% (1.3 ± 0.1 ng/ml) |
| 0.25 ppm | ~208% (2.7 ± 0.2 ng/ml) |
| 1 ppm | ~346% (4.5 ± 0.8 ng/ml) |
| 4 ppm | ~1254% (16.3 ± 2.6 ng/ml) |

The optimum increase in plasma $T_3$ level appears to be 50-150%, i.e. 150 to 250% of the normal level. Accordingly, when a $T_3$ analog is used, the dosage is preferably adjusted to provide a plasma thyroid hormone bioactivity level corresponding to 150-250% of the normal level. (It should be borne in mind that the normal exogenous plasma $T_3$ levels are in a rapid state of decline during the "finishing phase".) When the level of plasma thyroid hormone bioactivity is 360-1200%, body weight gain can be depressed by as much as 57%, and feed consumption can be depressed by as much as 35%; moreover, accretion of certain muscle protein (particularly breast muscle) is decreased, because the rate of protein breakdown greatly exceeds the rate of protein synthesis.

The fractional synthesis rate (FSR) of the pectoralis major (breast) muscle was increased ($p < 0.05$) by 56% in chickens fed 4 ppm of $T_3$ whereas this dose of $T_3$ increased the fractional degradation rate of breast muscle by 116%. A wide range of dietary $T_3$ doses (0.25 to 4 ppm of feed) increased ($p < 0.05$) the rate of protein synthesis in the leg muscle of broiler chickens by at least about 49%. The lower doses of $T_3$ (0.25 to 1 ppm) had only a slight effect upon protein synthesis rate in breast muscle, but these lower doses, particularly the 0.25 ppm dose, were much more desirable in terms of the Fractional Degradation Rate (FDR) of protein in breast muscle. Accordingly, Fractional Accretion Rate (FAR) in the pectoralis major (breast) muscle was affected negatively by $T_3$ doses in the 1 to 4 ppm range, whereas the effect was positive at the 0.25 ppm level. The positive effect upon FAR in leg muscle was better for the birds fed 0.25 ppm $T_3$ than the birds fed 1.0 or 4.0 ppm $T_3$. In fact the 0.25 ppm dose of $T_3$ increased the FAR of pectoralis major (breast muscle) by 88% and the FAR of leg muscle by 45% when compared to the control group. Therefore the lowest dose of $T_3$ (0.25 ppm) appears to be near optimal since this dose reduces abdominal fat weight by 22% while protein accretion in breast and leg muscle was increased by 45-88%.

Dietary $T_3$ administered according to this invention has now been found to decrease plasma GH levels and to alter plasma levels of insulin and glucagon. The lower GH levels observed in chickens fed 0.25 ppm $T_3$ do not appear to have a statistically significant effect upon final body weight, however.

Surprisingly, these data suggest that metabolically active thyroid hormone can be caused to be more important than GH levels in stimulating certain kinds of growth in chickens and maintaining a favorable protein turnover rate, particularly during the last part of the growth period. Significant loss of growth rate is observed when $T_3$ administration exceeds the guidelines set by this invention and can even be disastrous from the standpoint of marketability of the carcass or keeping the growth period sufficiently short for economic practicality. Significant loss of growth rate is also observed when the period of administering dietary $T_3$ extends too far back into the rapid growth part of the growth period.

When the guidelines discovered for this invention are observed, significant improvement in the body compositions of market-ready broiler chickens can be obtained solely through the administration of dietary metabolically-active thyroid hormone. Because of the convenience and economic attractiveness of this very simple hormone manipulation, the use of readily available metabolically active thyroid hormones (such as $T_3$) in the diet of broiler chickens (after the rapid growth phase is completed) is a particularly preferred embodiment of this invention.

Although this invention is not bound by any theory, one could theoretically describe this invention as a method for counteracting the rapid decline in endogenous $T_3$ levels during the "finishing phase" of the growth period of poultry, and by counteracting this decline with carefully timed and carefully measured doses of $T_3$, fat accretion is inhibited while favorable protein turnover is maintained or even improved. The high level of protein FAR is surprising in view of the tendency of $T_3$ to suppress GH levels (probably by inhibiting synthesis and secretion of GH by the pituitary gland).

A possible theoretical reason for the synergistic effect of $T_3$+GH or $T_3$+GH releasing factor (GRF) administration during the finishing phase is that bringing about an increase in endogenous GH or providing exogenous GH can partially or even fully counteract the lowering of the endogenous GH levels caused by the increased plasma thyroid hormone.

EXAMPLES

In the Examples which follow, the principle and practice of this invention are illustrated. To provide maximum scientific control over the results, cGH was administered by daily intramuscular injection even through this technique of administration would not normally be used in commercial practice. The following abbreviations are used in these Examples:

CF = control feed
$T_3$ = 3,3',5-triiodo-L-thyronine
$T_4$ = thyroxine
PTU = propylthiouracil
TRH = thyrotropin-releasing hormone
GH = growth hormone (e.g. ncGH, natural chicken GH)
BW = body weight
ADG = average daily weight gain
ADFC = average daily feed consumption
BI = bicarbonate buffer injection
N = number of test chickens
SEM = standard error of the mean

EXAMPLE 1

The Effect of Thyroid Manipulation and Chicken Growth Hormone Injections on Growth, Feed Efficiency and Body Composition of Broiler Cockerels

MATERIALS AND METHODS

The purpose of this study was to determine the effect manipulating blood levels of thyroid hormones and/or growth hormone on growth performance and body composition of broiler chickens. The following thyroid-active substances were purchased from Sigma Chemical Company (St. Louis, MO.): Product T 2877 (3,3',5-triiodo-L-thyronine or $T_3$), Product T 2376 (3-[4-(4-hydroxy-3,5-diiodophenoxy)-3,5-diiodophenyl]-L-alanine or $T_4$), Product P 9012 (L-pyroglutamyl-L-histidyl-L-prolinamide or TRH), and Product P 3755 (6-N-propyl-2-thiouracil or PTU). Purified natural chicken growth hormone (ncGH) was obtained from the Research and Education Center, Harbor-UCLA Medical Center, Torrance, Calif. A premix was prepared by thoroughly mixing the required quantity of thyroid-active substance (50 mg of $T_3$, 50 mg of $T_4$, 250 mg TRH) into 200 g of dextrose. The premix (200 g) was then used to prepare 50 kg batches of each experimental diet according to the formula for broiler-finisher ration described in Table 1. The diet containing 0.5% PTU was prepared by mixing 250 g of PTU into 49.75 kg of the basal ration (Table 1). The following dietary levels were thus achieved: 1 ppm $T_3$, 1 ppm $T_4$, 5 ppm TRH, 0.5% PTU, or control feed (CF).

Broiler cockerels (Ross X Arbor Acre strain) were raised to 3 weeks-of-age in a battery-brooder and then transferred to wire grow-out cages (4 birds/pen) held in two controlled-environment rooms (10 pens/room). Beginning at 3 weeks of age, eight birds (2 pens of 4 birds) were randomly assigned to each of 10 treatments. The chickens were provided the experimental diets and water ad libitum. The five dietary treatments (CF, $T_3$, $T_4$, TRH and PTU) were designated for convenience in presentation of data as Group 1. The remaining five treatments (Group 2) consisted of a dietary treatment (with the exception of PTU) plus a single daily intramuscular injection of 100 ug ncGH/kg body weight [i.e., CF+buffer injection (CF+BI), CF+GH, $T_3$+GH, $T_4$+GH, and TRH+GH]. For injection, the ncGH was reconstituted in sterile 0.025M sodium bicarbonate buffer (pH 9.8). The 10 treatments were administered for 21 days (i.e., from 3 to 6 weeks of age).

Measurement of body weight and feed consumption at weekly intervals allowed calculation of the average daily gain (ADG, g/bird/day), average daily feed consumption (ADFC, g/bird/day) and the feed-to-gain ratio (FIG, kg feed/kg gain) over the 21 day experimental period. Blood samples were taken each week (4, 5, and 6 weeks) just before (pre-injection) and 4 hours post-injection of ncGH. Specific radioimmunoassays were used to measure plasma levels of cGH (J. A. Proudman, *Proc. Soc. Exp. Biol. Med.* 175:417–419, 1984), $T_3$ and $T_4$ (L. A. Cogburn and R. M. Freeman, *Gen. Comp. Endocrinol.* 68:113–123, 1987), insulin and glucagon (P. C. Allen and J. P. McMurtry, *Poultry Sci.* 63:1129–1135, 1984). At the conclusion of the study, birds were killed and the carcasses frozen for proximate analysis. The frozen carcasses were ground in a meat grinder and aliquots of each ground carcass taken for determination of moisture, protein, fat and ash by established analytical procedures (*Official Method of Analysis*, Edition 13, W. Horwitz ed., Association of Official Analytical Chemist, Washington, D.C., 1980). Body composition data are presented as a percent of live weight at 6 weeks-of-age. Least squares regression analysis was used to test for significant differences (P<0.05) due treatment.

TABLE 1

| Composition of Broiler-Finisher Ration | |
|---|---|
| | % |
| Ingredients | |
| Corn, yellow, ground | 64.88 |
| Soybean meal, 48% | 21.23 |
| Poultry by-product meal | 3.50 |
| Corn gluten meal, 60% | 4.00 |
| Blended fat | 3.31 |
| Defluoridated phosphate | 1.71 |
| Limestone | 0.47 |
| Livestock salt (NaCl) | 0.170 |
| L-lysine | 0.070 |
| D,L-methionine | 0.060 |
| Trace mineral premix | 0.050 |
| Vitamin premix | 0.050 |
| Hormone/dextrose premix | 0.400 |
| Grand total | 100% |
| Analysis | |
| Protein | 20.7% |
| Fat | 6.5% |
| Fiber | 2.4% |

TABLE 1-continued

Composition of Broiler-Finisher Ration

| | % |
|---|---|
| Metabolizable Energy | 3244 kcal/kg |

RESULTS

Growth Performance

The final body weight of hypothyroid PTU-treated chickens was 18% lower (P<0.05) than that of birds fed CF or thyroid hormones (Table II). Although not significantly different, TRH-fed birds had a 6% higher body weight (BW), a 9% higher ADG and a 11% higher ADFC rate than the CF group. Dietary $T_3$ treatment did not affect growth rate or feed efficiency of broiler chickens. In contrast, hypothyroidism induced by dietary PTU depressed growth rate and reduced feed conversion. The combination of exogenous cGH treatment with dietary $T_3$ or $T_4$ reduced the final BW, ADG and ADFC by 12 to 15% when compared to the CF+BI group (Table III). Compared to the FTG ratio of the CF+BI group, feed efficiency was improved (P<0.05) by 9% in the CF+GH group and by 5% in the TRH+GH treatment.

TABLE II

Growth and Feed Efficiency of Broiler Cockerels Fed Thyroid-active Substances (Group 1)

| Treatment | BW (kg) | ADG | ADFC | FTG |
|---|---|---|---|---|
| CF | 1.74 ± 0.1$^a$ | 52.0 ± 2.1$^{ab}$ | 112.9 ± 0.7$^{ab}$ | 2.18 ± .10$^{ab}$ |
| $T_3$ 1 ppm | 1.70 ± .09$^a$ | 48.8 ± 4.3$^b$ | 101.1 ± 5.2$^b$ | 2.08 ± .08$^b$ |
| $T_3$ 1 ppm | 1.76 ± .04$^a$ | 51.9 ± 3.3$^{ab}$ | 108.4 ± 3.6$^b$ | 2.09 ± .06$^b$ |
| $T_4$ 5 ppm | 1.85 ± .08$^a$ | 56.5 ± 0.2$^a$ | 125.2 ± 5.5$^a$ | 2.21 ± 0.1$^{ab}$ |
| TRH 0.5% | 1.42 ± .05$^b$ | 39.2 ± 4.0$^c$ | 92.3 ± 7.9$^c$ | 2.36 ± .04$^a$ |
| PTU | | | | |

Means (±SEM) within a column possessing a different superscript are significantly (P < 0.05) different.

TABLE III

Growth and Feed Efficiency of Broiler Cockerels Fed Thyroid Active Substances and Injected Daily with ncGH (Group 2)

| Treatment | BW (kg) | ADG | ADFC | FTG |
|---|---|---|---|---|
| CF + BI | 1.77 ± .04$^a$ | 53.3 ± 1.3$^a$ | 118.4 ± 1.2$^a$ | 2.22 ± .08$^a$ |
| CF + GH | 1.83 ± .04$^a$ | 57.0 ± 0.4$^a$ | 115.8 ± 1.8$^{ab}$ | 2.03 ± .02$^c$ |
| $T_3$ + GH | 1.58 ± .06$^b$ | 46.2 ± 3.9$^b$ | 102.6 ± 6.7$^{bc}$ | 2.22 ± .04$^a$ |
| $T_4$ + GH | 1.54 ± .07$^b$ | 44.8 ± 0.6$^b$ | 97.7 ± 1.9$^c$ | 2.18 ± .01$^{ab}$ |
| TRH + GH | 1.75 ± .07$^{ab}$ | 53.5 ± 0.3$^a$ | 113.3 ± 1.2$^{ab}$ | 2.12 ± .01$^b$ |

Means (±SEM) within a column possessing a different superscript are significantly (P < 0.05) different.

Body Composition

The PTU treatment increased (P<0.05) body fat content by 50% at the expense of body ash, protein and water when compared to the CF group (Table IV). In contrast, dietary $T_3$ alone reduced body fat content by 17% while body protein and water were slightly increased. Dietary TRH increased body fat content by 12% although not significantly different from the CF birds. Dietary $T_3$ plus exogenous cGH treatment reduced (P<0.05) body fat content by 51% while the ash, protein and water content were increased by 6 to 9% above that of the CF+BI group (Table V). The combination of dietary $T_4$ and daily cGH injection improved body composition since body fat was reduced (P<0.05) by 26% when compared to the CF+BI group.

TABLE IV

Body Composition of Broiler Chickens Fed Thyroid-active Substances (Group 1)

| | | % BW | | | |
|---|---|---|---|---|---|
| Treatment | N | Water | Protein | Fat | Ash |
| CF | 8 | 66.4 ± .54$^b$ | 17.8 ± .46$^a$ | 12.1 ± .67$^{bc}$ | 2.32 ± .02$^{ab}$ |
| $T_3$ | 8 | 68.6 ± 1.0$^a$ | 18.4 ± .22$^a$ | 10.1 ± 1.2$^c$ | 2.19 ± .05$^{bc}$ |
| $T_4$ | 8 | 65.8 ± .29$^b$ | 18.2 ± .31$^a$ | 12.9 ± .41$^{bc}$ | 2.35 ± .03$^a$ |
| TRH | 8 | 65.5 ± .73$^b$ | 18.1 ± .21$^a$ | 13.6 ± .88$^b$ | 2.34 ± .06$^{ab}$ |
| PTU | 8 | 61.9 ± .73$^c$ | 17.2 ± .20$^b$ | 18.2 ± .80$^a$ | 2.17 ± .06$^c$ |

Means (±SEM) within a column possessing a different superscript are significantly (P < 0.05) different.

TABLE V

Body Composition of Broiler Chickens Fed Thyroid-active Substances and Injected Daily with ncGH (Group 2)

| | | % BW | | | |
|---|---|---|---|---|---|
| Treatment | N | Water | Protein | Fat | Ash |
| CF + BI | 8 | 64.7 ± .32$^c$ | 18.3 ± .18$^b$ | 14.6 ± .47$^a$ | 2.34 ± .05$^{ab}$ |
| CF + GH | 8 | 64.7 ± .51$^c$ | 18.1 ± .15$^b$ | 14.5 ± .52$^a$ | 2.20 ± .04$^b$ |
| $T_3$ + GH | 8 | 70.4 ± .46$^a$ | 19.3 ± .12$^a$ | 7.1 ± .57$^c$ | 2.51 ± .04$^a$ |
| $T_4$ + GH | 8 | 67.3 ± .46$^b$ | 18.6 ± .19$^b$ | 10.8 ± .57$^b$ | 2.47 ± .07$^{ab}$ |
| TRH + GH | 8 | 65.9 ± .62$^{bc}$ | 18.4 ± .11$^b$ | 13.0 ± .66$^a$ | 2.22 ± .06$^b$ |

Means (±SEM) within a column possessing a different superscript are significantly (P < 0.05) different.

Plasma Hormone Concentrations

The average plasma $T_3$ level of $T_3$-fed birds was 2.6-times higher (P<0.05) than that of birds in the CF, TRH or $T_4$ treatments (3 ng/ml) (Group 1). In contrast, the average $T_3$ level in the PTU-treated birds (1.5 ng/ml) was 53% lower (P<0.05) than the CF birds. Compared to the average of CF and TRH treatments, plasma $T_4$ levels were 9.6-times higher (P<0.05) in $T_4$-fed birds and reduced (P<0.05) by 58% in $T_3$-fed birds and by 76% in PTU-fed birds. Plasma GH levels were 1.9-times higher in PTU-fed birds and 32% lower in $T_3$-fed birds compared to the CF treatment. The plasma insulin/glucagon (I/G) molar ratio (i.e., increased glucagon and reduced insulin levels) of $T_3$-fed birds was 4.3-times lower (P<0.05) than that of CF birds (2.18) (Table VI). In contrast, the I/G molar ratio of PTU-treated birds was 2.9-times greater (P<0.05) than that of one CF group.

In Group 2, the average plasma GH concentration at 4 hours post-injection of 100 μg ncGH/kg BW (62 ng/ml) was 3-times higher (P<0.05) than the pre-injection GH concentration. The combination of daily cGH injection with dietary thyroid hormone reduced (P<0.05) the plasma I/G molar ratio by 6.8-fold in $T_3$-fed birds and by 2.2-fold in $T_4$-fed birds (Table VII). Clearly, these data indicate that elevated plasma $T_3$ levels inhibit insulin secretion whereas glucagon secretion is enhanced. The simultaneous elevation of cGH and $T_3$ levels in plasma potentiate this effect and lead to a dramatic reduction in deposition of body fat in broiler chickens.

TABLE VI

Plasma Concentration of Pancreatic Hormones in Broiler Chickens Fed Thyroid-active Substances (Group 1)

| Treatment | N | Insulin (I) pg/ml | Glucagon (G) pg/ml | I/G Molar Ratio |
|---|---|---|---|---|
| CF | 24 | $1038^b$ | $289^{ab}$ | $2.18^b$ |
| $T_3$ | 24 | $409^c$ | $491^a$ | $0.51^c$ |
| $T_4$ | 24 | $776^{bc}$ | $318^{ab}$ | $1.49^{bc}$ |
| TRH | 24 | $814^{bc}$ | $295^{ab}$ | $1.68^{bc}$ |
| PTU | 24 | $2349^a$ | $225^b$ | $6.35^a$ |

The I/G molar ratio was calculated from plasma insulin and glucagon levels in each plasma sample assuming molecular weights of 5734 for insulin and 3485 for glucagon.
Means (±SEM) within a column possessing a different superscript are significantly (P < 0.05) different.

TABLE VII

Plasma Concentration of Pancreatic Hormones in Broiler Chickens Fed Thyroid-active Substances and Injected Daily with ncGH (Group 2)

| Treatment | N | Insulin (I) pg/ml | Glucagon (G) pg/ml | I/G Molar Ratio |
|---|---|---|---|---|
| CF + BI | 24 | $1323^a$ | $313^b$ | $2.57^a$ |
| CF + GH | 24 | $1107^b$ | $298^b$ | $2.28^a$ |
| $T_3$ + GH | 24 | $249^d$ | $410^a$ | $0.38^c$ |
| $T_4$ + GH | 24 | $598^c$ | $314^b$ | $1.19^b$ |
| TRH + GH | 24 | $1047^b$ | $338^{ab}$ | $1.92^a$ |

Means (±SEM) within a column possessing a different superscript are significantly (P < 0.05) different.

EXAMPLE 2

The Effect of Dietary $T_3$ and ncGH Injection on Growth, Feed Efficiency, and Body Composition of Broiler Cockerels

Materials and Methods

The purpose of this study was to confirm the original finding of a synergism between exogenous cGH and dietary $T_3$ in reducing deposition of body fat in broiler chickens (Example 1). Forty-eight 3-week-old broiler cockerels (Ross X Arbor Acre) were randomly divided into four treatment groups that contained three pens of four birds. The birds were housed in a controlled-environment room under a 20 hour light/4 hour dark cycle with feed and water provided ad libitum. The four treatment groups were: control feed (CF)+buffer injection (BI), 1 ppm dietary $T_3$+BI, CF+GH injection (100 μg/kg BW/day), and 1 ppm dietary $T_3$+GH injection (100 μg/kg BW/day. The basal feed ration was formulated according to the ingredient composition in Table I.

The birds were continuously provided with CF or feed containing 1 ppm $T_3$ from 3 to 6 weeks-of-age. Each bird in the CF+GH and $T_3$+GH treatment groups received a single intramuscular injection of 100 μg ncGH/kg BW each day for 21 days. The preparation of ncGH used in this study was from the same lot used in Example 1. Birds in the CF+BI and $T_3$+BI treatments received a single intramuscular injection of 0.5 ml 0.025M sodium bicarbonate buffer (pH 9.8) each day for 21 days.

Body weights and feed consumption was determined at weekly intervals although the ADG, ADFC and FTG ratio was determined over the 21 day period. Blood samples were taken each week (4, 5 and 6 weeks-of-age) just before (pre-injection) and four hours post-injection of ncGH. At the conclusion of the study (6 weeks-of-age), birds were killed and the abdominal fat removed and weighed. The liver and abdominal fat were returned to the carcass which was frozen for proximate analysis as described in Example 1.

Results

The ADG, ADFC and FTG ratio was not affected by dietary $T_3$, daily ncGH injection or the combination of $T_3$+GH treatments (Table VIII). There was no significant effect of treatment on either the final (6 week) body weight or the relative liver weight (Table IX-A). However, dietary $T_3$ treatment alone reduced (P<0.05) the abdominal fat content by 28% whereas the combination of $T_3$+GH treatments was twice (P<0.05) as effective in reducing abdominal fat content (i.e., a 55% reduction). Daily injection of ncGH alone (CF+GH) did not affect growth performance, final body weight, relative liver weight or abdominal fat content. Body fat content (% BW) was reduced by 16% in $T_3$-fed birds and by 30% in birds given the $T_3$+GH treatment combination (Table IX-B). The body water and ash contents were also increased in birds treated with $T_3$ alone or in combination with GH injection.

The average plasma GH concentration at 4 hours post-injection of 100 μg ncGH/kg BW at 4, 5 and 6 weeks-of-age was 4-times higher than the pre-injection plasma GH levels. The average plasma $T_3$ level in the $T_3$+BI and $T_3$+GH treatment groups was 2.3-times higher than that of birds given the CF+BI or CF+GH treatment.

TABLE VIII

Growth and Feed Efficiency of Broiler Chickens Fed Triiodothyronine (T$_3$) and Injected Daily with ncGH

| Treatment | N | ADG | ADFC | FTG |
|---|---|---|---|---|
| CF + BI | 3 | 53.5 ± 0.5 | 118.5 ± 1.8 | 2.21 ± .02 |
| T$_3$ + BI | 3 | 52.6 ± 1.0 | 117.9 ± 0.8 | 2.24 ± 0.3 |
| CF + GH | 3 | 53.0 ± 2.8 | 115.4 ± 3.5 | 2.18 ± .05 |
| T$_3$ + GH | 3 | 49.5 ± 4.1 | 111.2 ± 6.0 | 2.26 ± .07 |

Each value represents the mean (±SEM) of three pens (4 birds/pen) over the three week experimental period (e.g., N = 3).

TABLE IX-A

Final Body Weight and Relative Weight (% BW) of the Liver and Abdominal Fat of Broiler Cockerels Fed Triiodothyronine (T$_3$) and Injected Daily with ncGH

| Treatment | N | Body Weight (BW, kg) | Liver (% BW) | Abdominal Fat (% BW) |
|---|---|---|---|---|
| CF + BI | 12 | 1.86 ± .060 | 2.91 ± .239 | 2.57 ± .129$^a$ |
| T$_3$ + BI | 12 | 1.86 ± .048 | 2.54 ± .096 | 1.86 ± .396$^b$ |
| CF + GH | 12 | 1.88 ± .051 | 2.74 ± .102 | 2.56 ± .178$^a$ |
| T$_3$ + GH | 12 | 1.77 ± .071 | 2.80 ± .059 | 1.16 ± .143$^c$ |

Means (±SEM) within a column possessing a different superscript are significantly (P < 0.05) different.

TABLE IX-B

Body Composition of Broiler Cockerels Fed Triiodothyronine (T$_3$) and Injected Daily with ncGH

| Treatment | N | % BW | | | |
|---|---|---|---|---|---|
| | | Water | Protein | Fat | Ash |
| CF + BI | 12 | 63.5 ± .34$^c$ | 17.2 ± .29 | 15.7 ± .33$^a$ | 2.31 ± .073$^{ab}$ |
| T$_3$ + BI | 12 | 65.5 ± .60$^b$ | 17.3 ± .36 | 13.2 ± .62$^b$ | 2.40 ± .054$^a$ |
| CF + GH | 12 | 63.7 ± .33$^{bc}$ | 17.0 ± .17 | 15.9 ± .32$^a$ | 2.23 ± .058$^b$ |
| T$_3$ + GH | 12 | 67.7 ± .46$^a$ | 17.2 ± .16 | 11.0 ± .54$^c$ | 2.39 ± .028$^a$ |

Means (±SEM) within a column possessing a different superscript are significantly (P < 0.05) different.

EXAMPLE 3

Effect of Dietary T$_3$ Alone, Administered at Various Dose Levels

Materials and Methods

Bird Management

Day-old broiler cockerels were randomly assigned to 24 pens (5 birds/pen) in a battery brooder. The total duration of the bird management period lasted from 7 to 8 weeks. Hereafter, the end of the first week of life of the birds is referred to as week no. 1 (i.e. 7 days of life), the end of the second week as week no. 2, etc. At week no. 3, four birds from each pen were transferred to wire grow-out cages. Four levels of T$_3$ (0, 0.25, 1 and 4 ppm) were fed from week no. 5 to week no. 7 (4 pens/treatment). Body weight and feed consumption were determined at weekly intervals. A 5 ml blood sample was obtained from each bird at week no. 7 and stored at −20° C. until assayed for plasma hormones.

At week no. 7 (49 days-of-age), one-half of the birds (8 birds/treatment) were killed for measurement of the abdominal fat pad and liver weights. The muscles were removed, weighed, frozen in liquid N$_2$ and stored at −20° C. until analyzed. At 51 days-of-age, groups of 4 birds per treatment were given a subcutaneous infusion of 4 μCi/Kg of 14C-L-tyrosine emulsified in sesame seed oil and immediately placed in metabolism cages. The expired CO$_2$ was trapped in 15 ml of scrubbing solution (1:2 ethanolamine/methyl cellusolve) and the tubes were changed every 15 minutes for 90 minutes. At 90 minutes, the birds were removed from the metabolism cages and blood was obtained via cardiac puncture. Birds were then sacrificed by cervical dislocation and the muscles were removed, weighed, frozen in liquid N$_2$ and stored at −20° C. until analyzed. Radioactivity in the samples containing trapped CO$_2$ was counted for 10 minutes using a liquid scintillation spectrophotometer. At 54 days-of-age, groups of 4 birds per treatment were killed, the muscles were dissected, weighed, and frozen until analyzed.

TISSUE PREPARATION

The right breast muscle, i.e. BM (*Pectoralis major*) and right leg muscles, i.e. LM (gastrocnemius and *peroneus longus*) were dissected out from the birds, weighed and immediately frozen in liquid nitrogen and stored at −20° C. until analyzed for tyrosine content as specific radioactivity of tyrosine. All muscle tissues were analyzed for protein content; only tissues from isotope experiments were analyzed for tyrosine content as specific radioactivity of tyrosine.

Hormone Assays

Equilibrium, double antibodies radioimmunoassays (RIA) were used to determine plasma levels of chicken growth hormone (GH) according to Proudman, Proc. Soc. Exp. Biol. Med. 175:417 (1984), glucagon according to Allen et al, Poult. Sci. 63:1129 (1984) and thyroxine, according to Cogburn et al, Gen. Comp. Endocrinol. 68:113 (1987). Plasma insulin was quantified by using nonequilibrium RIA described by McMurtry et al., Poult. Sci. 62:697 (1983). The molar ratio of insulin and glucagon (I/G) was calculated from plasma insulin and glucagon concentrations in each sample, assuming molecular weights of 5734 for insulin and 3485 for glucagon. Plasma level of insulin-like growth factor-I (IGF-I) was determined by heterologous RIA in accordance with McGuinness. ("Relationship between Plasma Insulin-Like Growth Factor and Growth Hormone Levels . . . ", M. S. Thesis, University of Delaware, Newark, Del., 1989).

Protein Turnover Measurement

Protein turnover rate was determined by measuring the Fractional Synthesis Rate (FSR) and Fractional Accretion Rate (FAR); the Fractional Degradation Rate was obtained by the difference of FSR and FAR (FAR=FSR−FDR). FAR of breast muscle and leg muscles were estimated from regression of total muscle protein on age. Total muscle protein was determined by multiplying the muscle weight by protein content. Protein content was determined by the Biuret method. The slope obtained by linear regression was the absolute rate of protein accretion (g/d). The FAR (%/d) was calculated by dividing the absolute accretion rate by the average muscle protein at 51 days-of-age. The FSR (ks) was calculated according to the equation described by Garlick et al., Biochem. J. 136:935 (1973). Protein-bound tyrosine in muscle tissue was separated from free tyrosine according to the procedures of Laurent et al. Biochem. J. 176:419 (1978) with some modification. Approximately 1 g of muscle tissue was homogenized with 5 ml cold distilled water and washed with 15 ml of cold 5% trichloroacetic acid (TCA). The homogenate was then centrifuged for 15 min at 4000×g. The supernatant containing the free tyrosine was poured off and the TCA was extracted with 15 ml of diethyl ether. The supernatant was concentrated to dryness. The dried sample was dissolved in 5 ml of distilled water and stored at 4° C. until analyzed for tyrosine content and the specific radioactivity of tyrosine.

The pellet was extracted with 15 ml of hot 5% TCA, 15 ml of 3:1 ethanol/diethyl ether (v/v) and 20 ml of diethyl ether. The washed pellet was then placed in a 25×150 mm test tube with screw cap and hydrolyzed in 15 ml of 6N hydrochloric acid (HCl) for 16 hours at 125° C. The hydrolysate was concentrated to dryness. The dried sample was dissolved in 5 ml of distilled water and stored at 4° C. until analyzed for tyrosine content and specific radioactivity of tyrosine.

Tyrosine Analysis

Tyrosine content in free tyrosine (supernatant) and the protein-bound fraction (hydrolysate) was analyzed according to the method of Udenfriend et al, J. Biol. Sci. 196:227 (1952).

Specific Radioactivity of Tyrosine

The specific radioactivity of tyrosine in the protein-bound fraction (hydrolysate) and in the free tyrosine (supernatant) was analyzed using the method described by Schaefer et al, Can. J. Anim. Sci. 62:1223 (1982). One ml of the samples were added into 10 ml of aquasol and counted for 10 minutes in a liquid scintillation spectrophotometer.

Statistical Analyses

Data were analyzed by analysis of variance for a randomized complete-block design. Data for ADG, ADFC and FTG were based on pen average. Unless otherwise indicated, data used for analysis was obtained from individual birds. Difference among treatments were tested by Fisher's protected LSD method.

RESULTS

Growth Performance

Among graded doses of $T_3$ treatments (Table 1), average daily gain (ADG) was the highest ($p<0.05$) in the control group. Decreasing ADG was associated with increasing $T_3$ dose; however, the decrease in 0.25 ppm-fed birds was not significant. Dietary $T_3$ at 4.0 ppm level depressed average daily feed consumption (ADFC) and gain to feed ratio (GTF) by 35% ($p<0.05$) and 33% ($p<0.05$), respectively. Lower $T_3$ levels (0.25 and 1.0 ppm) did not affect the ADFC and GTF. Both final body weight (BW) and abdominal fat weight (Table 2) were decreased as dietary $T_3$ dose increased with the exception of 0.25 ppm fed birds in which the reduction was not significant. The greatest reduction in BW was 22.2% ($p<0.05$) observed in birds fed 4.0 ppm $T_3$. Dietary $T_3$ at 0.25, 1.0 and 4.0 ppm levels dramatically reduced the abdominal fat weights by 22.2% ($p<0.05$), 26.6% ($p<0.05$) and 63.3% ($p<0.05$), respectively. The relative weights (% BW) of liver weight (RLW), right breast muscle (RBM) and right leg muscle (RLM) were not different among treatments.

Muscle Protein Turnover

In order to determine if the 14C-tyrosine in the free amino acids pool reached an equilibrium after injection with isotope, radioactivity in expired $CO_2$ was monitored for 90 minutes after the injection. A plateau level of expired $14C-CO_2$ which is an indication of achieving isotopic equilibrium, was maintained after 30 minutes of infusion of radio-labelled tyrosine.

Table 3 provides the values for fractional synthesis rate (FSR), fractional degradation rate (FDR) and fractional accretion rate (FAR) of protein in breast muscle and leg muscles of broiler chickens fed graded doses of $T_3$ from week no. 5 to week no. 7. All dietary $T_3$ doses increased the FSR of protein in leg muscles by 44% to 53% ($p<0.05$), while only the highest dose of $T_3$ (4.0 ppm) enhanced the FSR of protein in breast muscle by 55.7% ($p<0.05$). Higher dietary levels of $T_3$ (1.0 and 4.0 ppm) appeared to increase FDR about 2-3 fold in both breast muscle and leg muscles. The observed enhanced FSR of the muscles of 1.0 and 4.0 ppm-fed birds were not great enough to accomplish the elevated FDR (except leg muscles of 4.0 ppm-fed birds); therefore, the resulting FAR values were negative, indicating a loss of muscle protein. Higher FAR values of protein were observed in both breast muscle (4.9 %/d) and leg muscles (9.3 %/d) of 0.25 ppm fed-birds. Both FSR and FDR of leg muscles were increased by dietary treatment of 0.25 ppm $T_3$; however, the increased rate of synthesis was greater than that of degradation rate. The overall protein turnover rate of breast muscle of 0.25 ppm-fed birds did not differ from that of control birds.

Plasma Hormone Levels

Plasma GH levels were found to be decreased ($p<0.05$) by treatment of dietary $T_3$ at all levels while plasma IGF-1 level was only reduced ($p<0.05$) by the 4.0 ppm level (Table 4). Administration of dietary $T_3$ at 0.25, 1.0 and 4.0 ppm levels showed a dose-dependent elevation ($p<0.05$) of plasma levels $T_3$ by a factor of from 2.1-fold (0.25 ppm $T_3$) up to 12.6-fold (4 ppm $T_3$). Plasma $T_4$ levels were decreased 67% ($p<0.05$) by the $T_3$ treatment disregarding the dose regardless of dose level (Table 4). Dietary $T_3$ also altered plasma levels of insulin and glucagon with a consequential change in insulin/glucagon (I/G) molar ratio (Table 5). Plasma insulin levels in 0.25 ppm, 1.0 ppm and 4.0 ppm $T_3$ treated birds were reduced by 27%, 60% ($p<0.05$) and 68% ($p<0.05$), respectively. On the other hand, dietary $T_3$ at 0.25 ppm, 1.0 and 4.0 ppm levels increased glucagon secretion by 16%, 44% ($p<0.05$) and 46% ($p<0.05$). Although the changes in plasma insulin and glucagon levels in birds fed 0.25 ppm $T_3$ were not significantly different from the control group, the I/G ratio was reduced by 31% ($p<0.05$) because the changes in hormone concentration were in opposite direction. The I/G molar ratio of chickens fed either 1 or 4 ppm of $T_3$ was reduced ($p<0.05$) by 70-76% when compared to the control chickens.

This Example appears to establish that a >20% reduction in abdominal fat can be achieved with no treatment beyond the simple administration of 0.25 ppm dietary $T_3$, with no significant adverse effect in final body weight. Still greater reductions in abdominal fat can be achieved with dietary $T_3$ alone at the 1.0/level of parts per million of feed (ppm), but not without significant sacrifice of final body weight. The 4.0 ppm dose level of $T_3$ appears to cause an excessive loss of final body weight which would probably not be commercially acceptable.

TABLE 1
GROWTH PERFORMANCE OF BROILER CHICKENS FED GRADED DOSES OF $T_3$ FROM WEEK NO. 5 TO WEEK NO. 7*

| $T_3$ dose, ppm of feed | Average Daily Gain (g) | Average Daily Feed Consumption (g) | Gain-To-Feed Ratio |
|---|---|---|---|
| 0 | 69.6 ± 1.3$^a$ | 153.9 ± 1.8$^a$ | 0.452 ± .008$^a$ |
| 0.25 | 66.5 ± 6.0$^{ab}$ | 150.2 ± 10.0$^a$ | 0.441 ± .014$^{ab}$ |
| 1.0 | 57.0 ± 3.0$^b$ | 139.0 ± 4.6$^a$ | 0.409 ± 0.01$^b$ |
| 4.0 | 30.0 ± 1.1$^c$ | 99.5 ± 1.7$^b$ | 0.302 ± .013$^c$ |

*NOTES TO TABLE:
Means within a column possessing a different superscript are significantly (p < 0.05) different.
Estimates of average daily gain, average daily feed consumption and gain-to-feed ratio are based on four pens (4 birds/pen) over the two week experimental period.

TABLE 2
FINAL BODY WEIGHT (Kg) AND RELATIVE WEIGHTS (% BW) OF LIVER (RLW), ABDOMINAL FAT, RIGHT PECTORALIS MAJOR (RPM), RIGHT LEG MUSCLE 1 (RLM) OF BROILER CHICKENS FED GRADED DOSES OF $T_3$ FROM WEEK NO. 5 TO WEEK NO. 7*

| $T_3$ dose, ppm of feed | BW (Kg) | RLW (% BW) | Abdom. Fat (% BW) | RBM (% BW) | RLM (% BW) |
|---|---|---|---|---|---|
| 0 | 2.56$^a$ | 2.52$^a$ | 2.56$^a$ | 5.30$^a$ | 0.74$^a$ |
| 0.25 | 2.42$^{ab}$ | 2.24$^a$ | 1.99$^{ab}$ | 5.60$^a$ | 0.71$^a$ |
| 1.0 | 2.33$^b$ | 2.14$^a$ | 1.88$^b$ | 5.36$^a$ | 0.76$^a$ |
| 4.0 | 1.99$^c$ | 2.18$^a$ | 0.94$^c$ | 5.81$^a$ | 0.75$^a$ |

*NOTES TO TABLE:
Leg muscles consisted of the gastrocnemius and peroneus longus.
Means within a column possessing a different superscript are significantly (p < 0.05) different. The number of birds in each dosage group was 8.

TABLE 3
FRACTIONAL SYNTHESIS RATE, FRACTIONAL DEGRADATION RATE AND FRACTIONAL ACCRETION RATE OF BREAST MUSCLE AND LEG MUSCLES OF BROILER CHICKENS FED GRADED DOSES OF $T_3$ FROM WEEK NO. 5 TO WEEK NO. 7

| | Dietary $T_3$ (ppm of feed) | | | |
|---|---|---|---|---|
| | 0 | 0.25 | 1.0 | 4.0 |
| FSR$^{1, 2}$ (%/d) | | | | |
| Pectoralis major | 15.6 ± 0.9$^b$ | 17.2 ± 1.3$^b$ | 18.2 ± 1.7$^b$ | 24.3 ± 1.4$^a$ |
| Leg muscles 3 | 15.3 ± 0.6$^b$ | 22.0 ± 2.1$^a$ | 22.1 ± 1.9$^a$ | 23.4 ± 0.8$^a$ |
| FRD$^4$ (%/d) | | | | |
| Pectoralis major | 13.0 | 12.3 | 22.7 | 28.1 |
| Leg muscles 3 | 8.9 | 13.6 | 24.1 | 18.4 |
| FAR$^5$ (%/d) | | | | |
| Pectoralis major | 2.6 | 4.9 | −4.5 | −3.8 |
| Leg muscles | 6.4 | 9.3 | −2.0 | 5.0 |

$^1$means within a row possessing a different superscript are significantly (p < 0.05) different.
$^2$Number (N) of birds in each group = 4 except for 4.0 ppm group (N = 2).
$^3$Leg muscles consisted of the gastrocnemius and peroneus longus.
$^4$FDR = FSR - FAR.
$^5$Calculated by linear regression from data of subgroups of birds killed on second day before (N = 4) and the day of isotope injection (N = 4).

TABLE 4
PLASMA GH, IGF-1, $T_3$ AND $T_4$ LEVELS OF BROILER CHICKENS GIVEN GRADED DOSES OF DIETARY $T_3$* from 5 to 7 weeks of age.

| $T_3$ Dose (ppm of feed) | GH (ng/ml) | IGF-I (ng eg/ml) | $T_3$ (ng/ml) | $T_4$ (ng/ml) |
|---|---|---|---|---|
| 0 | 3.5 ± 0.4$^a$ | 115.0 ± 7.8$^a$ | 1.3 ± 0.1$^c$ | 10.8 ± 0.8$^a$ |
| 0.25 | 2.0 ± 0.4$^b$ | 100.7 ± 2.9$^a$ | 2.7 ± 0.2$^b$ | 6.3 ± 0.6$^b$ |
| 1.0 | 2.1 ± 0.4$^b$ | 97.7 ± 6.3$^a$ | 4.5 ± 0.8$^b$ | 6.2 ± 0.6$^b$ |
| 4.0 | 1.8 ± 0.2$^b$ | 58.8 ± 8.2$^b$ | 16.3 ± 2.6$^a$ | 5.1 ± 0.8$^b$ |

*NOTES TO TABLE:
Means within a column possessing a different superscript are significantly (p < 0.05) different.
Plasma hormone levels represent the average of 8 birds per treatment.

TABLE 5
PLASMA INSULIN AND GLUCAGON LEVELS AND INSULIN TO GLUCAGON MOLAR RATIO (I/G RATIO) OF BROILER COCKERELS GIVEN GRADED DOSES OF DIETARY $T_3$ from 5 to 7 weeks of age.

| $T_3$ Dose (ppm of feed) | Insulin (pg/ml) | Glucagon (pg/ml) | I/G Ratio |
|---|---|---|---|
| 0 | 1,062 ± 48$^a$ | 566 ± 38$^c$ | 1.17 ± 0.9$^a$ |
| 0.25 | 772 ± 155$^{ab}$ | 656 ± 75$^{bc}$ | 0.81 ± .20$^b$ |
| 1.0 | 426 ± 65$^{bc}$ | 816 ± 64$^{ab}$ | 0.35 ± .06$^c$ |
| 4.0 | 344 ± 92$^c$ | 824 ± 61$^a$ | 0.28 ± .08$^c$ |

Means within a column possessing a different superscript are significantly (P < 0.05) different.

What is claimed is:

1. A method for lowering the extent of fat deposition in living poultry grown substantially for meat production, during the normal growth cycle of the poultry, without detracting substantially from the growth rate, which comprises:
providing exogenous metabolically-active thyroid hormone to the living poultry during the finishing phase of the normal growth cycle of the poultry, said providing of the exogenous metabolically-active thyroid hormone being delayed until the poultry are at least about 3 weeks of age, the exogenous metabolically-active thyroid hormone having at least about 50% of the receptor-binding capacity of 3,3'5-triiodo-L-thyronine, and the dosage of exogenous metabolically-active thyroid hormone being sufficient to provide a level of plasma thyroid hormone level which has about 150 to about 250% of the bioactivity of the normal endogenous level of 3,3',5-triodo-L-thyronine.

2. A method according to claim 1 wherein the metabolically-active thyroid hormone is exogenous 3,3',5-triiodo-L-thyronine, and the said hormone is orally administered to the poultry.

3. A method according to claim 2, wherein the said hormone is fed to poultry in the finishing feed formula, in the amount of at least about 0.1 to 1 part per million based on the weight of a daily ration of feed.

4. A method according to claim 3, wherein said amount is about 0.1 to 0.5 parts per million, on the same basis.

5. A method according to claim 1, wherein the poultry are treated in accordance with the said method for about two to five weeks.

6. A method according to claim 5 wherein the poultry are broiler chickens having normal or enhanced pituitary function, wherein the body fat content of the broiler chicken is decreased as a result of said method by at least about 15% by weight, compared to untreated broiler chickens.

7. A method for lowering the extent of fat deposition in living poultry, grown substantially for meat production, having normal or enhanced pituitary function, during the normal growth cycle of the poultry, without detracting from the normal growth rate, which consists essentially of:

(a) waiting until the poultry are at least three weeks of age and then feeding to the poultry a finishing feed formula containing at least about 0.01 but less than 3 parts per million, based on the weight of the feed, of a metabolically-active thyroid hormone of the formula

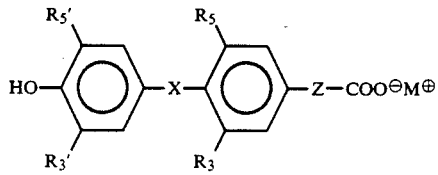

(1)

wherein X is O, S, or $CH_2$,

Z is $C_2$–$C_4$ alkylene or amino-substituted $C_2$–$C_4$ alkylene, $M^+$ is a physiologically acceptable cation, $R_3$ and $R_5$ are H or iodo, at least one of them being iodo, $R_3'$ and $R_5'$ are iodo, or hydrogen or —A—COO—$M^+$, where A is $C_2$–$C_4$ alkylene and $M^+$ is a physiologically acceptable cation, provided, that when $R_3'$, $R_5'$, $R_3$ and $R_5$ are all iodo, then Z—COO$^-$ is the residue of the anion of acetic or propionic acid; said thyroid hormone having at least about 50% of the receptor-binding capacity of 3,3',5-triiodo-L-thyronine.

8. A method according to claim 7, wherein the feed formula contains about 0.01 to 1 part per million of said hormone, on the same basis.

9. A method according to claim 8, wherein the said hormone is 3,3',5-triiodo-L-thyronine, and the feed formula contains about 0.1 to 0.5 part per million of said hormone, on the same basis.

* * * * *